June 11, 1957 E. S. BOERNER Plant Pat. 1,609
CHRYSANTHEMUM PLANT
Filed Oct. 26, 1956
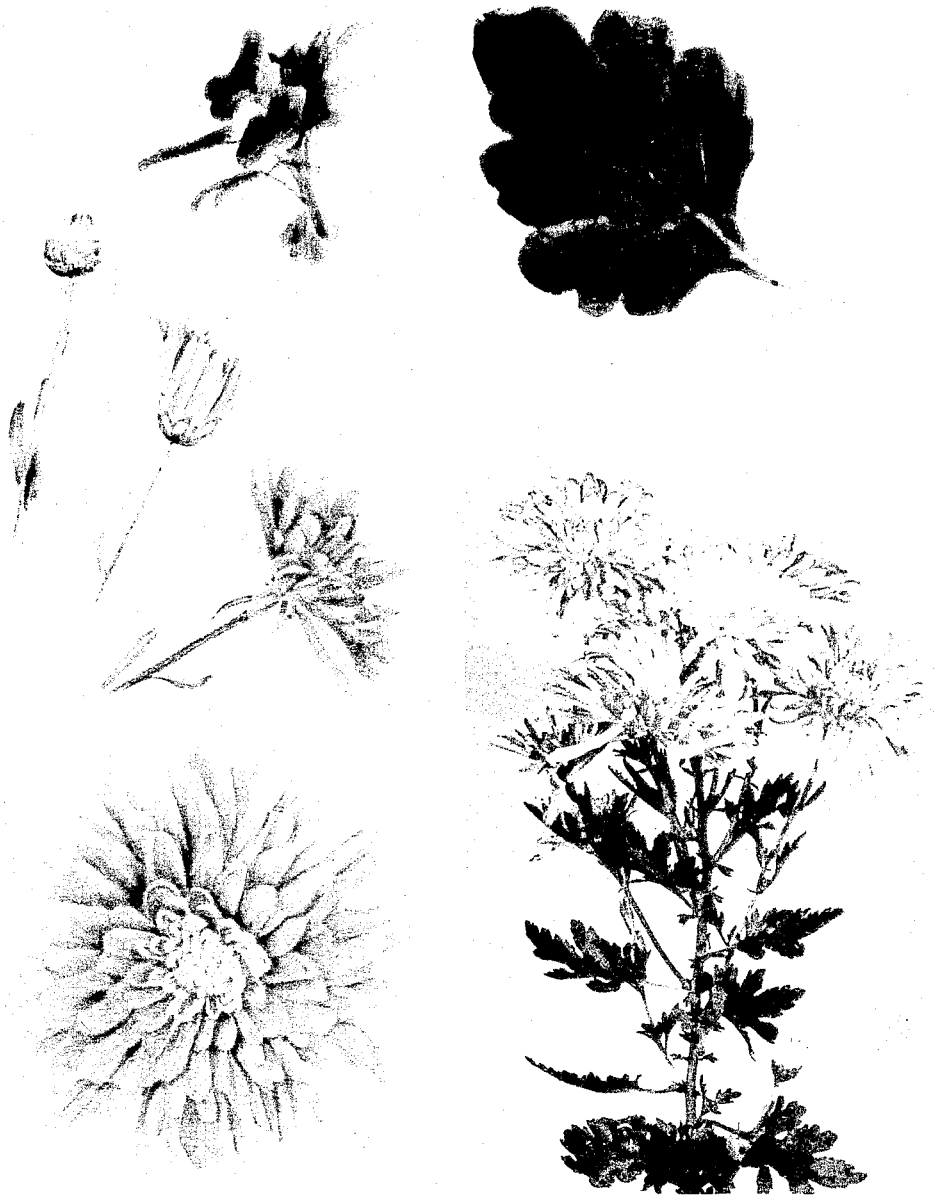
Inventor.
E. S. Boerner
By: Robb & Robb
attorneys.

United States Patent Office

Plant Pat. 1,609
Patented June 11, 1957

1,609

CHRYSANTHEMUM PLANT

Eugene S. Boerner, Newark, N. Y., assignor to Jackson & Perkins Company, Newark, N. Y., a corporation of New York Application October 26, 1956, Serial No. 618,663

1 Claim. (Cl. 47—60)

The present invention relates to a new and distinct variety of chrysanthemum plant of the decorative class which was originated by me by crossing the variety "Fred Rockwell" (Plant Patent No. 718) with an unnamed and unpatented large-flowered Hortorum seedling.

The primary objective of this cross was to produce a new chrysanthemum variety having the same type of plant as the parent "Fred Rockwell" and which bears flowers of substantially the same color as this parent, but the flowers of which are larger in size. This objective was fully achieved, along with other improvements, as evidenced by the following characteristics which are outstanding in the new variety:

(1) A plant form corresponding to that of "Fred Rockwell";

(2) Foliage of Dark Cress Green color and leathery texture;

(3) An early blooming habit, usually beginning about September 5;

(4) Large flowers; and (5) A general color tonality of the flowers corresponding to Coral Red, lightly overcast with Scarlet Red.

The foregoing characteristics and distinctions definitely differentiate my new variety from its parents, as well as from all other varieties of its class, and asexual reproduction of the new variety by both top cuttings and also by underground runners, as performed at Newark, New York, shows that these characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character, as well as a typical specimen plant, depicted in black-and-white, which is illustrative of the form and habit of growth of the plant.

The following is a detailed description of my new variety, with color terminology in accordance with Ridgway's Color Standards and Nomenclature:

Parentage: "Fred Rockwell" × an unnamed, large-flowered Hortorum seedling.

Classification: Decorative.

Growth: Vigorous; attains a height of approximately 2½ feet.

Cold resistance: Winter-hardy in northern New York, and flowers are very frost-resistant.

Blooming period: In the Newark, New York, climatic area, blooming usually commences about September 5 and continues until heavy frosts.

*Flower*

(Observations made from specimens grown in a field at Newark, New York, in the early part of September, and in the early afternoon.)

Bud:

*Color.*—When sepals first divide—Dark Vinaceous, Plate 27. When petals begin to unfurl—Antimony Yellow, Plate 15, lightly overcast with Nopal Red, Plate 1. When half-blown: inside of petals—Nopal Red, Plate 1; reverse of petals—Capucine Orange, Plate 3, lightly overcast with Coral Red, Plate 13.

*Peduncle.*—Color—Light Cress Green, Plate 31. Strength—strong.

Bloom:

*Size.*—4½ inches.

*Stem.*—Long; strong.

*Form.*—Decorative.

*Petalage.*—Double.

*Color.*—Center of flower—Scarlet, Plate 1, lightly overcast with Brazil Red, Plate 1. Outer petals—Scarlet, Plate 1, lightly overcast with Coral Red, Plate 13. Base of petals—Sulphur Yellow, Plate 5. Inside of petals—Coral Red, Plate 13, lightly overcast with Scarlet, Plate 1. Reverse of petals—Pale Yellow Orange, Plate 3, lightly overcast with Peach Red, Plate 1.

*Petals.*—Texture—medium. Form—long pointed.

*Fragrance.*—Characteristic chrysanthemum.

*Plant*

Form: Upright, with long stems breaking from the ground; with clusters of flowers only at the top of the stem; no branches appearing.

Growth: Free.

Foliage:

*Size.*—Medium.

*Quantity.*—Normal.

*Color.*—Upper side—Dark Cress Green, Plate 31. Reverse side—Cress Green, Plate 31.

*Texture.*—Leathery.

I claim:

A new and distinct variety of chrysanthemum plant of the decorative type, substantially as herein shown and described, characterized particularly as to novelty by a plant form substantially corresponding to that of the variety "Fred Rockwell" (Plant Patent No. 718), its leathery Dark Cress Green foliage, its relatively early blooming habit, its relatively large flowers, and the distinctive Coral Red, lightly overcast with Scarlet, general color tonality of its flowers.

No references cited.